United States Patent [19]

Cauwet et al.

[11] Patent Number: 5,747,014
[45] Date of Patent: May 5, 1998

[54] COSMETICS COMPOSITIONS CONTAINING AT LEAST ONE ANIONIC SURACANT OF ALKYLGALACTOSIDE URONATE TYPE AND AT LEAST ONE AMPHOTERIC POLYMER

[75] Inventors: Daniele Cauwet, Paris; Claude Dubief, Le Chesnay, both of France

[73] Assignee: L'Oreal, Paris, France

[21] Appl. No.: 912,754

[22] Filed: Aug. 18, 1997

Related U.S. Application Data

[63] Continuation of Ser. No. 537,939, filed as PCT/FR94/00631, May 31, 1994, abandoned.

[30] Foreign Application Priority Data

Jun. 1, 1993 [FR] France .................................. 93 06530

[51] Int. Cl.$^6$ ....................................................... A61K 7/50
[52] U.S. Cl. ...................... 424/70.11; 424/70.21; 424/70.22; 424/70.17

[58] Field of Search ............................ 424/70.11, 70.21, 424/70.17, 70.22

[56] References Cited

U.S. PATENT DOCUMENTS 5,501,812   3/1996   Vermeer et al. .................... 252/174.17

FOREIGN PATENT DOCUMENTS 0 532 370   3/1993   European Pat. Off. .

*Primary Examiner*—Margaret W. Glass
*Attorney, Agent, or Firm*—Jacobson, Price, Holman & Stern, PLLC

[57] ABSTRACT

The present invention relates to hair treating compositions which contain, in an aqueous medium, both an anionic surfactant of an alkyl galactoside uronate type and an polymeric amphoteric surfactant.

19 Claims, No Drawings

COSMETICS COMPOSITIONS CONTAINING AT LEAST ONE ANIONIC SURACANT OF ALKYLGALACTOSIDE URONATE TYPE AND AT LEAST ONE AMPHOTERIC POLYMER

This application is a continuation of application Ser. No. 08/537,939, filed Nov. 8, 1995, now abandoned, which is a 371 of PCT/FR94/00631 filed May 31, 1994.

The invention relates to cosmetic compositions containing at least one anionic surfactant of alkylgalactoside uronate type and at least one amphoteric polymer and to cosmetic treatment processes for keratinous substances using such compositions.

Compositions for washing the hair or the skin are generally formulated from anionic or nonionic surfactants or their mixtures, optionally in the presence of amphoteric surfactants.

Hair attacked by atmospheric agents such as light or chemical treatments and washed with conventional washing compositions is difficult to disentangle and this disadvantage is found to be further accentuated in the case of fine hair.

Compositions for washing the hair which use these anionic or nonionic surfactants alone do not lead to good cosmetic properties; in particular, the disentangling of wet hair is difficult and the shaping and the hold of the hairstyle with time are not satisfactory.

Anionic surfactants of alkylgalactoside uronate type have already been recommended it washing compositions for the hair. They have been described in Patent Application EP 0,532,370.

The Applicant Company has just surprisingly discovered that the combination, in washing and/or treating compositions for keratinous substances, of an anionic surfactant of alkylgalactoside uronate type and of an amphoteric polymer confers improved disentangling properties, in particular for wet hair, on these compositions.

In addition, this combination confers hold and body on dry hair, as well as liveliness on curly hair.

The subject of the present invention is therefore cosmetic compositions containing at least one anionic surfactant of alkylgalactoside uronate type and at least one amphoteric polymer.

Another subject of the invention consists of the use of these compositions for treating and/or washing keratinous substances such as the hair or the skin.

Another subject relates to cosmetic treatment processes for the hair or for the skin by means of the compositions of the invention; washing and treatment processes for the hair being preferred.

The cosmetic compositions according to the invention contain, in a cosmetically acceptable aqueous medium, at least one anionic surfactant of alkylgalactoside uronate type and at least one amphoteric polymer.

The alkylgalactoside uronates which can be used in accordance with the invention correspond to the is following formula (I):

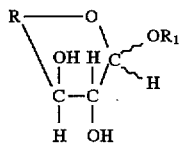

in which:

$R_1$ denotes a linear or branched alkyl radical containing 8 to 22 carbon atoms, R denotes the group

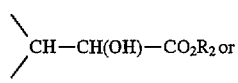  (i)

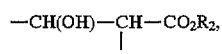  (ii)

in which the carbon carrying the hydroxyl group is connected to the endocyclic oxygen atom; $R_2$ is a hydrogen atom, an alkali metal, and alkaline-earth metal, a quaternary ammonium group which is unsubstituted or substituted by alkyl or hydroxyalkyl radicals or an amino acid quaternary ammonium group.

The alkali metal is in particular sodium or potassium and the alkaline-earth metal is preferably magnesium. Mention may be made, as quaternary ammonium salts, of the salts of ammonia, triethanolamine, monoethanolamine, 2-amino-2-methyl-1,3-propanediol and 2-amino-2-methyl-1-propanol; the amino acid is in particular histidine, arginine or lysine.

Use is preferably made of the compounds of formula (I) in which the $R_1$ radical denotes a $C_8$–$C_{14}$ alkyl and more particularly the decyl radical.

Use is in particular made of the following compounds:

Sodium decyl α-D-galactopyranoside uronate:

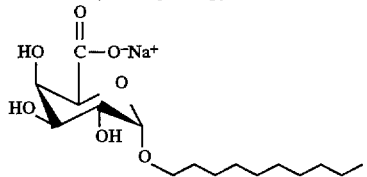

Sodium decyl β-D-galactopyranoside uronate:

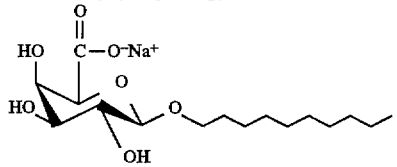

Sodium decyl α-D-galactofuranoside uronate:

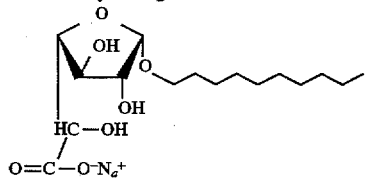

Sodium decyl β-D-galactofuranoside uronate:

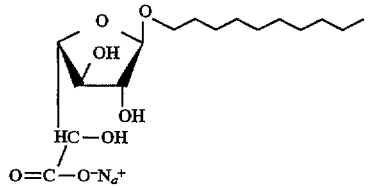

The amphoteric polymers which can be used in accordance with the invention are chosen from polymers containing units A and B distributed statistically in the polymer chain, where A denotes a unit deriving from a monomer containing at least one basic nitrogen atom and B denotes a unit deriving from an acidic monomer containing one or more carboxyl or sulfonic groups or else A and B can denote groups deriving from carboxybetaine or sulfobetaine zwitterionic monomers;

A and B can also denote a cationic polymer chain containing primary, secondary, tertiary or quaternary amine groups, in which chain at least one of the amine groups carries a carboxyl or sulfonic group connected via a hydrocarbon radical or else A and B form part of a chain of a polymer containing an ethylene-α,β-dicarboxyl unit in which one of the carboxyl groups has been brought to react with a polyamine containing one or more primary or secondary amine groups.

The more particularly preferred amphoteric polymers corresponding to the definition stated above are chosen from the following polymers:

(1) polymers resulting from the copolymerization of a vinyl compound carrying a carboxyl group, such as more particularly acrylic acid, methacrylic acid, maleic acid and alpha-chloroacrylic acid, and of a basic substituted vinyl compound containing at least one basic nitrogen atom, such as more particularly dialkylaminoalkyl methacrylate and acrylate and dialkylaminoalkylmethacrylamide and -acrylamide. Such compounds are described in U.S. Pat. No. 3,836,537.

(2) polymers resulting from the polymerization of a quaternary diallyldialkylammonium monomer and at least one anionic monomer, such as polymers containing approximately 60 to approximately 99% by weight of units derived from a quaternary diallyldialkylammonium monomer in which the alkyl groups are chosen independently from alkyl groups having 1 to 18 carbon atoms and in which the anion is an anion of an acid having an ionization constant of greater than $10^{-13}$ and 1 to 40% by weight of this polymer of an anionic monomer chosen from acrylic or methacrylic acids, the molecular weight of this polymer being between approximately 50,000 and 10,000,000, determined by gel permeation chromatography. Such polymers are described in Application EP-A-269,243.

Preferred polymers are, inter alia, polymers containing alkyl groups chosen from groups having 1 to 4 carbon atoms and more particularly methyl and ethyl groups.

Among these polymers, copolymers of dimethyldiallylammonium or diethyldiallylammonium chloride and of acrylic acid are particularly preferred. These polymers are, for example, sold under the names "Merquat 280" and "Merquat 295" by the Company Merck.

It is also possible to use the dimethyldiallylammonium chloride-acrylic acid-acrylamide terpolymers sold under the name "Merquat Plus 3330" by the Company Merck.

(3) polymers resulting from the copolymerization of
  a) from at least one monomer selected from acrylamides and methacrylamides substituted on the nitrogen with an alkyl radical,
  b) at least one acidic comonomer containing one or more reactive carboxyl groups, and
  c) at least one basic comonomer, such as esters containing primary, secondary, tertiary and quaternary amine substituents of acrylic and methacrylic acids and the product of quaternization of dimethylaminoethyl methacrylate with dimethyl or diethyl sulfate.

More particularly preferred N-substituted acrylamides or methacrylamides according to the invention are the groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides. The acidic comonomers are more particularly chosen from acrylic, methacrylic, crotonic, itaconic, maleic and fumaric acids, as well as monoalkyl esters, the alkyl group having 1 to 4 carbon atoms, of maleic acid or of fumaric acid.

The preferred basic comonomers are aminoethyl, butylaminoethyl, N,N'-dimethylaminoethyl and N-tert-butylaminoethyl methacrylates.

(4) polyaminoamides, partially or completely crosslinked and alkylated, comprising units of general formula:

in which $R_7$ represents a divalent radical selected from saturated dicarboxylic acid radicals, mono- or dicarboxylic aliphatic acid radicals containing an ethylenic double bond, an ester of these acids with a lower alkanol having 1 to 6 carbon atoms and radicals resulting from the addition reaction of any one of the said acids with a bis-primary or bis-secondary amine, and Z denotes a radical of a polyalkylenepoly(bis-primary or mono- or bis-secondary amine) and preferably represents:

a) in proportions of 60 to 100 mol %, the radical

in which either x=2 and n=2 or 3 or x=3 and n=2;

b) in proportions of 0 to 40 mol %, the above radical (III) in which x=2 and n=1, or the radical of formula:

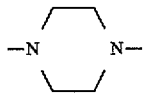

c) in proportions of 0 to 20 mol %, the radical —NH—$(CH_2)_6$—NH—, these polyaminoamides being crosslinked by addition of a bifunctional crosslinking agent chosen from epihalohydrines, diepoxides, dianhydrides and bis-unsaturated derivatives, by means of 0.025 to 0.35 mol of crosslinking agent per amine group of the polyaminoamide and alkylated by the action of acrylic acid, chloroacetic acid or an alkanesulfone or their salts.

The saturated carboxylic acids are preferably chosen from acids having 6 to 10 carbon atoms, such as adipic, 2,2,4- and 2,4,4-trimethyladipic or terephthalic acid and acids containing an ethylenic double bond such as, for example, acrylic, methacrylic and itaconic acids.

The alkanesulfones used in the alkylation are preferably propane- or butanesulfone and the salts of the alkylating agents are preferably the sodium or potassium salts.

(5) polymers containing zwitterionic units of formula:

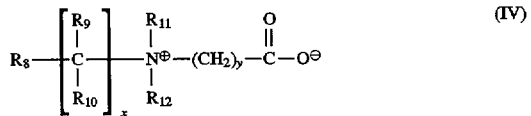

in which $R_8$ denotes a polymerizable unsaturated group such as an acrylate, methacrylate, acrylamide or methacrylamide group, x and y represent an integer from 1 to 3, $R_9$ and $R_{10}$ represent hydrogen, methyl, ethyl or propyl, and $R_{11}$ and $R_{12}$ represent a hydrogen atom or an alkyl radical such that the sum of the carbon atoms in $R_{11}$ and $R_{12}$ does not exceed 10.

The polymers comprising such units can also contain units derived from nonzwitterionic monomers such as vinylpyrrolidone, dimethyl- or diethylaminoethyl acrylate or methacrylate, alkyl acrylates or methacrylates, acrylamides or methacrylamides or vinyl acetate.

Mention may be made, by way of example, of the methyl methacrylate-methyl dimethylcarboxymethyl-ammonioethyl methacrylate copolymer.

(6) polymers containing monomer units corresponding to the following formulae:

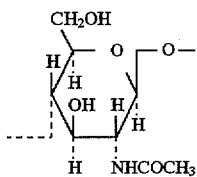
(A)

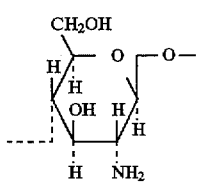
(B)

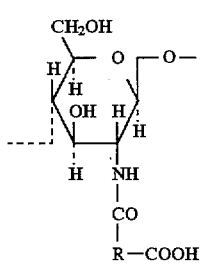
(C)

in which the A unit is present in proportions of between 0 and 30%, B is present in proportions of between 5 and 50% and C is present in proportions of between 30 and 90%. In the formula C, R represents a radical of formula:

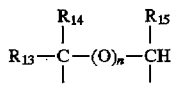

in which, if $n=0$, $R_{13}$, $R_{14}$ and $R_{15}$, which are identical or different, each represent a hydrogen atom, a methyl, hydroxyl, an acetoxy residue, amino residue, a monoalkylamine residue or a dialkylamine residue, optionally interrupted by one or more nitrogen atoms and/or optionally substituted with one or more amine, hydroxyl, carboxyl, alkylthio or sulfonic groups, or an alkylthio residue in which the alkyl group carries an amino residue, at least one of the radicals $R_{13}$, $R_{14}$ and $R_{15}$ in this case being a hydrogen atom; or, if $n=1$, $R_{13}$, $R_{14}$ and $R_{15}$ each represent a hydrogen atom, as well as the salts formed by these compounds with bases or acids.

(7) polymers resulting from the N-carboxyalkylation of chitosan, such as the N-carboxymethylchitosan or the N-carboxybutylchitosan sold under the name "Evalsan" by the Company Jan Dekker.

(8) polymers corresponding to the general formula (V) are described in French Patent 1,400,366:

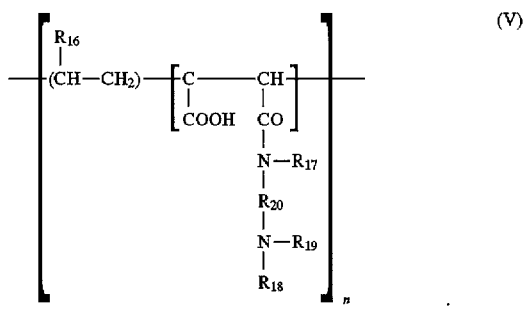
(V)

in which $R_{16}$ represents a hydrogen atom or a $CH_3O$, $CH_3CH_2O$ or phenyl radical, $R_{17}$ denotes hydrogen or a lower alkyl radical such as methyl or ethyl, $R_{18}$ denotes hydrogen or a lower alkyl radical such as methyl or ethyl, and $R_{19}$ denotes a lower alkyl radical such as methyl or ethyl or a radical corresponding to the formula: $-R_{20}-N(R_{18})_2$, $R_{20}$ representing a group

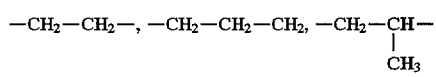

$R_{18}$ having the meanings mentioned above, as well as the higher homologs of these radicals containing up to 6 carbon atoms.

(9) amphoteric polymers of the -A-Z-A-Z type chosen from
  a) polymers obtained by the action of chloroacetic acid or sodium chloroacetate on compounds containing at least one unit of the formula:

$$-A-Z-A-Z-A-  \quad (VI)$$

where A denotes a radical

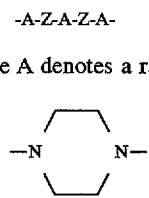

and Z is a divalent radical B or B', said divalent radical B and B' which are identical or different, are a straight- or branched-chain alkylene radical containing up to 7 carbon atoms in the main chain, which chain is unsubstituted or substituted with hydroxyl groups, and which can contain, in addition, oxygen, nitrogen and sulfur atoms and 1 to 3 aromatic and/or heterocyclic rings; the oxygen, nitrogen and sulfur atoms being present in the form of an ether, thioether, sulfoxide, sulfone, sulfonium, alkylamine, alkenylamine, hydroxyl, benzylamine, amine oxide, quaternary ammonium, amide, imide, alcohol, ester or urethane group.

b) Polymers of formula -A-Z-A-Z- (VI) where A is a radical

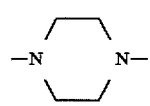

where Z is a divalent radical B or B', at least one Z being a divalent radical B'; B having the meaning stated above and B' is a divalent radical which is a straight- or branched-chain alkylene radical having up to 7 carbon atoms in the main chain, which radical is unsubstituted or substituted with one or more hydroxyl radicals and which contains one or more nitrogen atoms, the nitrogen atom being substituted with an alkyl chain optionally interrupted by an oxygen atom and necessarily containing one or more carboxyl functional groups and one or more hydroxyl functional groups, and converted to a betaine by reaction with chloroacetic acid or sodium chloroacetate.

The alkylgalactoside uronates of formula (I) are present in the compositions in accordance with the invention in proportions preferably of between 1 and 50% by weight with respect to the total weight of the composition.

The amphoteric polymers defined above are present in proportions of between 0.01 and 10% by weight with respect to the total weight of the composition.

If the compositions according to the invention are not used for washing keratinous substances, the total concentration of anionic surfactants of formula (I) is between 1 and 10% and more particularly between 1 and 5% by weight with respect to the total weight of the composition. These compositions are used in particular as compositions to be rinsed or not to be rinsed, applied before or after shampooing, dyeing, bleaching, perming or hair straightening, in a composition for dyeing, bleaching, perming or straightening hair.

When the compositions according to the invention are washing compositions, they contain the surfactants of formula (I) in a total concentration of between 4 and 50% by weight and preferably between 8 and 40% by weight with respect to the total weight of the composition.

The compositions can contain, in addition to the alkylgalactoside uronate, other cosurfactants of anionic, nonionic, amphoteric, zwitterionic or cationic nature.

Among the anionic surfactants, there may be mentioned the alkali metal salts, the ammonium salts, the amine salts, the aminoalcohol salts or the magnesium salts of the following compounds: fatty acids, alkyl sulfates, alkyl ether sulfates, alkylamidoether sulfates, alkylarylpolyether sulfates, monoglyceride sulfates, alkylsulfonates, alkylethersulfonates, alkylamidesulfonates, alkylarylsulfonates, olefinsulfonates, paraffinsulfonates, alkylsulfosuccinates, alkylethersulfosuccinates, alkylamidesulfosuccinates, the alkylsulfosuccinamates, alkylsulfoacetates, the alkyl ether phosphate, acylsarcosinates, N-acyltaurates, and acylglutamates or isethionates.

The alkyl or acyl radical of these various compounds generally consists of a carbon chain containing from 10 to 20 carbon atoms.

It is also possible to use weakly anionic surfactants, such as the polyoxyalkylenated alkyl amide or alkyl ether carboxylic acids, such as those containing 2 to 50 ethylene oxide groups.

The nonionic surfactants are more particularly chosen from the alcohols or the α-diols or the alkylphenols or the polyethoxylated or polypropoxylated fatty acids, with a fatty chain containing 8 to 18 carbon atoms, the number of ethylene oxide or propylene oxide groups being between 2 and 50 and the number of glycerol groups being between 2 and 30.

It is more particularly possible to mention the copolymers of ethylene oxide and of propylene oxide; the condensates of ethylene oxide and of propylene oxide with fatty alcohols; the polyethoxylated fatty amides having preferably 2 to 30 mol of ethylene oxide; the polyethoxylated fatty amines having preferably 2 to 30 mol of ethylene oxide; the oxyethylenated fatty acid esters of sorbitan having preferably 2 to 30 mol of ethylene oxide; the fatty acid esters of sugar, the fatty acid esters of polyethylene glycol, the fatty acid esters of glycols, the amine oxides such as the oxides of ($C_{10}$–$C_{14}$)-alkylamines or of N-acylamidopropylmorpholine.

The preferred amphoteric or zwitterionic surfactants are the derivatives of secondary or tertiary aliphatic amines, in which the aliphatic radical is a linear or branched chain containing 8 to 18 carbon atoms and which contains at least one water-solubilizing carboxylate, sulfonate, sulfate, phosphate or phosphonate anionic group; the ($C_8$–$C_{20}$) alkylbetaines, the sulfobetaines, the ($C_8$–$C_{20}$)alkylamido ($C_1$–$C_6$)alkylbetaines or the ($C_8$–$C_{20}$)alkylamido($C_1$–$C_6$) alkylsulfobetaines.

It is also possible to mention the alkylpeptides or the alkylimidazolium betaines.

Among the amine derivatives, there may be mentioned the products marketed under the name "Miranol", such as those described in the U.S. Pat. Nos. 2,528,378 and 2,781, 354 or listed in the CTFA dictionary, 3rd edition, 1982, under the names of Amphocarboxyglycinates or of Amphocarboxypropionates.

The cationic surfactants are chosen from the quaternary ammonium salts, such as the ($C_8$–$C_{22}$) alkyltrimethylammonium halides, the ($C_8$–$C_{22}$) dialkyldimethylammonium halides or the ($C_8$–$C_{22}$) alkyldimethyl-hydroxyethylammonium halides.

The additional cosurfactants can represent up to 50% of the total weight of the surfactants present in the composition.

The pH of the compositions in accordance with the invention is generally between 2 and 10.5 and more particularly between 3 and 8.

Insofar as the cosmetically acceptable medium of the composition according to the invention is an aqueous medium, it may consist solely of water or of a mixture of water and of a cosmetically acceptable solvent, such as $C_1$–$C_4$ lower alcohols, such as ethanol, isopropanol or n-butanol; alkylene glycols, such as propylene glycol, or glycol ethers.

The compositions in accordance with the invention can be provided in various forms, such as a more or less thickened liquid, a gel, a solid bar, an emulsion (milk or cream), an aqueous/alcoholic lotion or a dispersion, and optionally be packaged as an aerosol and be dispersed in the form of a foam.

The compositions are, for example, emollient lotions, milks or creams, lotions, milks or creams for caring for keratinous substances, make-up removal creams or milks, foundation bases, antisun lotions, milks or creams, lotions, milks or creams for artificial tanning, shaving creams or foams, aftershave lotions, face masks, make-up products for the eyes, colors and foundations for the face, shampoos, bath or shower products, compositions to be rinsed or not to be rinsed, to be applied before or after shampooing, dyeing, bleaching, perming or hair straightening, or compositions for dyeing, bleaching, perming or straightening the hair.

The compositions in accordance with the invention can also contain, in addition, various additives such as thickening agents, such as polyacrylic acids, cellulose derivatives or esters of fatty acids and of polyethylene glycol, sequestering agents, foam reinforcers, preservatives, fragrances, electrolytes, fatty substances, such as fatty alcohols, ceramides or mineral, vegetable, animal or synthetic oils or waxes, UV screening agents, agents for combating free radicals, pearlescence agents, biocides, antibacterials, antidandruff agents, antiseborrheic agents, antiparasitic agents, repellents, dyes, pigments, oxidizing agents, reducing agents, moisturizers, anionic, nonionic or cationic polymers, vitamins or α-hydroxy acids.

Treatment of the keratinous substances is carried out by application to these substances of a cosmetically acceptable amount of a composition as defined above.

The process for washing and/or for conditioning the keratinous substances and in particular the hair in accordance with the invention consists in applying at least one composition as defined above to these substances, this application optionally being followed by a stage of rinsing with water.

The washing compositions can be used as shampoos but also as shower gels for washing the hair and the skin, in which case they are applied to the wet skin and hair, which are rinsed after application.

When the compositions are used for conditioning the hair, they are applied to the wet hair, after which the hair is either dried or, after an exposure time of 1 to 10 minutes, it is rinsed with water. It is observed that the wet hair disentangles readily, that the shaping of the hairstyle is made easier and that the latter has good hold with time.

The examples which follow are intended to illustrate the invention without having any limiting nature whatsoever.

EXAMPLE 1
SHAMPOO

| | |
|---|---|
| Sodium decyl D-galactoside uronate | 25 g |
| N-Octylacrylamide-methyl methacrylate-hydroxypropyl methacrylate-acrylic acid-tert-butylaminoethyl methacrylate copolymer, containing 100% AM, sold under the name of "Amphomer" by the company National Starch | 1 g |
| water q.s. for | 100 g |
| pH adjusted to 7.5 with NaOH | |

EXAMPLE 2
SHAMPOO

| | |
|---|---|
| Sodium decyl D-galactoside uronate | 15 g |
| Cocoylbetaine, as a 32% sol. | 5 g AM |
| Oxyethylenated and oxypropylenated diurethane of alcohols ($C_{16}/C_{18}$), containing 100% AM, "Dapral T 212" (Akzo) | 3 g |
| ($C_1$–$C_{18}$)Alkyl methacrylate-methacryloyl-betaine copolymer - 50% sol. (EtOH), "Amersette" (Mitsubishi) | 1 g |
| water q.s. for | 100 g |
| pH adjusted to 6.5 with HCl | |

EXAMPLE 3
SHAMPOO

| | |
|---|---|
| Sodium decyl D-galactoside uronate | 15 g AM |
| Cocoylbetaine as an aqueous solution containing 32% AM | 3 g AM |
| Chitosan derivative consisting of units | |

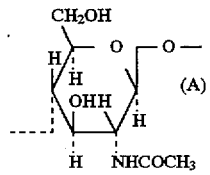
(A)

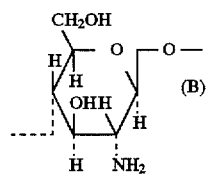
(B)

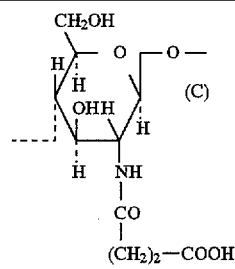
(C)

in the proportions (by weight)  A = 0 to 20%
B = 40 to 50%
C = 40 to 50%

EXAMPLE 4
CONDITIONER

| | |
|---|---|
| Sodium decyl D-galactoside uronate | 2 g AM |
| Dimethyldiallylammonium chloride-acrylic acid (80/20) copolymer as a 35% aqueous solution sold under the name of "Merquat 280" by the Company Merck | 5 g AM |
| Dye, fragrance, preservative | |
| water q.s. for | 100 g |
| pH adjusted to 7 with NaOH | |

We claim:
1. Hair treating cosmetic composition in the form of a thickened liquid, a gel, an emulsion, and aqueous/alcoholic lotion or a dispersion comprising, in a cosmetically acceptable aqueous medium
   (A) at least one anionic surfactant of alkylgalactoside uronate type of formula

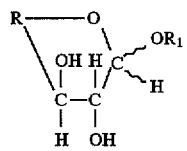 (I)

wherein $R_1$ denotes a linear or branched alkyl radical containing 8 to 22 carbon atoms,
R denotes a group

 (i)

 (ii)

in which the carbon carrying the hydroxyl group is connected to the endocyclic oxygen atom; $R_2$ is a hydrogen atom, an alkali metal, an alkaline-earth metal, a quaternary ammonium group which is unsubstituted or substituted by alkyls or hydroxyalkyls or an amino acid quaternary ammonium group, and
   (B) at least one amphoteric polymer containing units A and B distributed statistically in the polymer chain, said at least one amphoteric polymer being selected from a group of polymers consisting of:
      (i) polymers in which A is a monomer unit containing at least one basic nitrogen atom and B is an acid monomer unit containing one or more carboxyl or sulfonic groups;
      (ii) polymers in which A and B are carboxy betaine or sulfobetaine zwitterionic monomer units;
      (iii) polymers in which A and B are cationic polymer chains containing primary, secondary, tertiary or quaternary amine groups, in which chains at least one of the amine groups carries a carboxylic or sulfonic group linked via a hydrocarbon radical; and (iv) polymers in which A and B form part of a chain of a polymer containing an ethylene-α,β-dicarboxylic unit in which one of the carboxyl groups has been reacted with a polyamine containing one or more primary or secondary amine groups.

2. Composition according to claim 1, wherein, in formula (I), radical $R_2$ is selected from the group consisting of sodium, potassium, magnesium, and a quaternary ammonium group.

3. Composition according to claim 1, wherein $R_1$ is a $C_8$–$C_{14}$ alkyl.

4. Composition according to claim 1, wherein $R_1$ is a decyl radical.

5. Composition according to claim 4, wherein the compound of formula (I) is sodium decyl α-D-galactopyranoside uronate, sodium decyl β-D-galactopyranoside uronate, sodium decyl α-D-galactofuranoside uronate, or sodium decyl β-D-galactofuranoside uronate.

6. Composition according to claim 1, wherein the amphoteric polymers are selected from the group consisting of:

(1) polymers resulting from the copolymerization of a vinyl compound carrying a carboxyl group and a basic substituted vinyl compound containing at least one basic nitrogen atom;

(2) polymers resulting from the polymerization of a quarternary dialkyldialkylammonium monomer and at least one anionic monomer;

(3) polymers resulting from the copolymerization of
  a) at least one monomer being acrylamides or methacrylamides substituted on the nitrogen with an alkyl radical,
  b) at least one acidic comonomer containing one or more reactive carboxyl groups, and
  c) at least one basic comonomer;

(4) polyaminoamides, partially or completely cross-linked and alkylated, comprising units of general formula:

(II)

in which $R_7$ is a divalent radical selected from the group consisting of saturated dicarboxylic acid radicals, mono- or dicarboxylic aliphatic acid radicals containing an ethylenic double bond, $C_1$–$C_6$ alkyl esters of these acids and radicals resulting from the addition reaction to any one of said acids of a bis-primary or bis-secondary amine, and Z is a polyalkylene poly(bis-primary or mono- or bis-secondary amine) radical, these polyaminoamides being cross-linked by means of a bifunctional cross-linking agent being epihalohydrines, diepoxides, dianhydrides or bis-unsaturated derivatives, said cross-linking agent being used in an amount of 0.025 to 0.35 mol per amine group of the polyaminoamide and said polyaminoamide being alkylated by the action of acrylic acid, chloroacetic acid, an alkane sulfone or their salts;

(5) polymer containing zwitterionic units of formula:

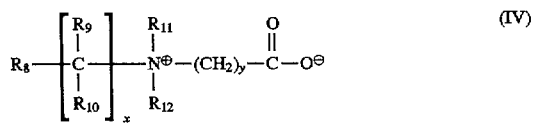

(IV)

in which $R_8$ is a polymerizable unsaturated group, x and y represent an integer from 1 to 3, $R_9$ and $R_{10}$ represent hydrogen, methyl, ethyl or propyl, and $R_{11}$ and $R_{12}$ represent a hydrogen atom or an alkyl radical with the proviso that the sum of the carbon atoms in $R_{11}$ and $R_{12}$ does not exceed 10;

(6) polymers containing 0 to 30% of units A of formula

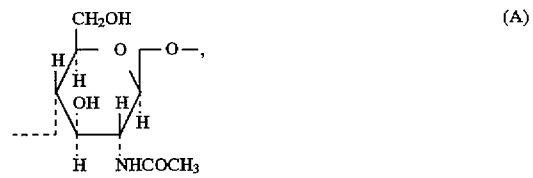

(A)

5 to 50% of units B of formula

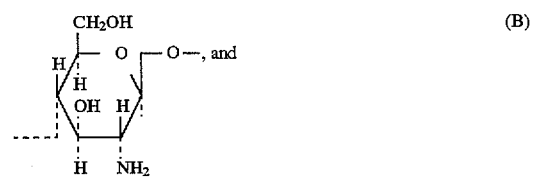

(B)

30 to 50% of units C of formula

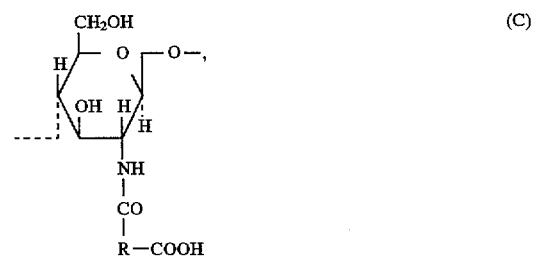

(C)

wherein in formula C, R represents a radical of formula

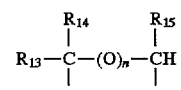

in which n is 0 or 1 and, when n=0, $R_{13}$, $R_{14}$ and $R_{15}$, which are identical or different, are selected from the group consisting of hydrogen atom, methyl, hydroxyl, acetoxy or amino residues, monoalkylamine residues, dialkylamine residues, optionally interrupted by one or more nitrogen atoms and/or optionally substituted with one or more amine, hydroxyl, carboxyl, alkylthio or sulfonic groups, and alkylthio residues in which the alkyl group carries an amino residue, at least one of the radicals $R_{13}$, $R_{14}$ and $R_{15}$ in this case being a hydrogen atom; and when n=1, $R_{13}$, $R_{14}$ and $R_{15}$ each represent a hydrogen atom;

(7) polymers resulting from the N-carboxyalkylation of chitosan;

(8) polymers corresponding to the general formula (V):

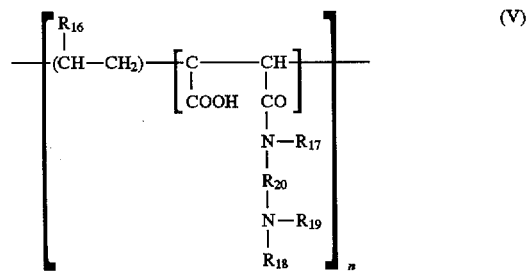

(V)

in which $R_{16}$ represents a hydrogen atom, $CH_3O$, $CH_3CH_2O$ or a phenyl radical, $R_{17}$ is hydrogen or lower alkyl radical, $R_{18}$ is hydrogen or a $C_1$–$C_6$ alkyl radical, and $R_{19}$ is a lower alkyl radial or a radical corresponding to the formula: —$R_{20}$—$N(R_{18})_2$, wherein $R_{20}$ is

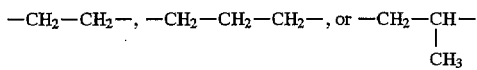

(9) amphoteric polymers type chose selected from the group consisting of
a) polymers obtained by the action of chloroacetic acid or sodium chloroacetate on compounds containing at least one unit of the formula:

-A-Z-A-Z-A- (VI)

where A is a radical

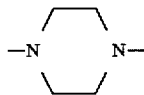

in which Z is a divalent radical B or B', said radicals B and B', which are identical or different, being straight- or branched-chain alkylene radicals containing up to 7 carbon atoms in the main chain, which chain is unsubstituted or substituted with hydroxyl groups, and which can contain, in addition, oxygen, nitrogen and sulfur atoms and 1 to 3 aromatic and/or heterocyclic rings; the oxygen, nitrogen and sulfur atoms when present being in the form of an ether, thioether, sulfoxide, sulfone, sulfonium, alkylamine, alkenylamine, hydroxyl, benzylamine, amine oxide, quaternary ammonium, amide, imide, alcohol, ester or urethane groups;

b) polymers of formula -A-Z-A-Z- (VI) where A is a radical

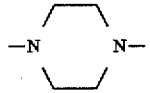

where Z is a divalent radical B or B', at least one being B'; B having the meaning stated above and B' is a divalent radical which is a straight- or branched-chain alkylene radical having up to 7 carbon atoms in the main chain, which chain is unsubstituted or substituted with one or more hydroxyl radicals and which contains one or more nitrogen atoms, the nitrogen atom being substituted with an alkyl chain optionally interrupted by an oxygen atom and necessarily containing one or more carboxyl functional groups and one or more hydroxyl functional groups, and converted to a betaine by reaction with chloracetic acid or sodium chloroacetate.

7. Composition according to claim 6, wherein
in polymers (1), the carboxyl group carried by the vinyl compound is selected from acrylic acid, methacrylic acid, maleic acid, and alpha-chloroacrylic acid;
in polymers (2), 60 to 99% by weight of the polymer units are quaternary diallyl dialkyl ammonium units in which the alkyl groups have 1 to 18 carbons and in which the anion is an anion of an acid having an ionization constant greater than $10^{-13}$ and 1 to 40% by weight of the units are anionic acrylic or methacrylic acid units, said polymers having a molecular weight ranging from 50,000 to 100,000 as determined by gel permeation chromatography;

in polymers (3), said basic comonomer c) is selected from esters of acrylic and methacrylic acids containing primary, secondary, tertiary, and quaternary amine substituents and products of quaternization of diemethylaminoethylmethacrylate with dimethyl or diethylsulfate;

in polyaminoamides (4), 60 to 100 mole % of the Z radicals have formula:

—NH—$(CH_2)_x$—NH— (III)

in which either x=2 and n=2 or 3 or x=3 and n=2, 0 to 40 mol % of the Z radicals have formula (III) above in which x=2 and n=1 or formula

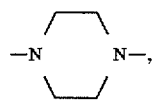

and 0 to 20 mol % of the Z radicals are —NH(CH2)$_6$—NH—; and in polymers (5), said polymers further contain non-zwitterionic units from vinylpyrrolidone, alkylacrylates or methacrylates, diethylaminoethylacrylate or methacrylate, acrylamides or methacrylamides, or vinylacetate.

8. Composition according to claim 1, wherein the anionic surfactants of formula (I) are present in proportions of between 1 and 50% by weight and the amphoteric polymers are present in proportions of between 0.01 and 10%, the percentages by weight being expressed with respect to the total weight of the composition.

9. Composition for conditioning keratinous substances according to claim 1, wherein the concentration of anionic surfactants of formula (I) is between 1 and 10% by weight with respect to the total weight of the composition.

10. Composition for washing keratinous substances according to claim 1, wherein the concentration of anionic surfactants of formula (I) is between 4 and 50% by weight with respect to the total weight of the composition.

11. Composition according to claim 1, wherein the composition contains an additional surfactant which is of anionic, nonionic, amphoteric, zwitterionic or cationic different from the surfactants of formula (I), in a proportion ranging up to 50% of the total weight of the surfactants present in the composition.

12. Composition according to claim 11, wherein the additional anionic surfactant is alkali metal salts, ammonium salts, amine salts, aminoalcohol salts, magnesium salts of the following compounds: fatty acids, alkyl sulfates, alkyl ether sulfates, alkylamidoether sulfates, alkylarylpolyether sulfates, monoglyceride sulfates, alkylsulfonates, alkylethersulfonates, alkyamidesulfonates, alkylarylsulfonates, olefinsulfonates, paraffinsulfonates, alkylsulfosuccinates, alkylethersulfosuccinates, alkylamidesulfosuccinates, alkylsulfosuccinamates, alkylsulfoacetates, alkyl ether phosphates, acylsarcosinates, N-acyltaurates or isethionates; the alkyl or acyl radical consisting of a carbon chain containing from 10 to 20 carbon atoms; isethionates; the alkyl or acyl radical consisting of a carbon chain containing from 10 to 20 carbon atoms; polyoxyalkylenated alkyl amide or alkyl ether carboxylic acids.

13. Composition according to claim 11, wherein the additional nonionic surfactant is alcohols, α-diols, alkylphenols, polyethoxylated or polypropoxylated fatty acids, with a fatty chain containing 8 to 18 carbon atoms, the number of ethylene oxide or propylene oxide groups being between 2 and 50 and the number of glycerol groups being between 2 and 30, copolymers of ethylene oxide and of propylene oxide, condensates of ethylene oxide and propylene oxide with fatty alcohols, polyethoxylated fatty amides, polyethoxylated fatty amines, oxyethylenated fatty acid esters of sorbitan, fatty acid esters of sugar, fatty acid esters of glycols or amine oxides.

14. Composition according to claim 11, wherein the additional amphoteric surfactant is from secondary or tertiary aliphatic amines, in which the aliphatic radical is a linear or branched chain containing 8 to 18 carbon atoms and which contains at least one water-solubilizing carboxylate, sulfonate, sulfate, phosphate or phosphonate anionic group; the $(C_8-C_{20})$alkylbetaines, the sulfobetaines, the $(C_8-C_{20})$-alkylamino$(C_1-C_6)$alkylbetaines, the $(C_8-C_{20})$-alkylamido$(C_1-C_6)$-alkylsulfobetaines; the alkylpeptides; or the alkylimidazolium betaines.

15. Composition according to claim 11, wherein the additional surfactant is selected from the quaternary ammonium salts.

16. Composition according to claim 1, wherein the cosmetically acceptable medium consists of water or a mixture of water and a cosmetically acceptable solvent.

17. Composition according to claim 1, in the form of a thickened liquid, a gel, an emulsion, and aqueous/alcoholic lotion, a dispersion or an aerosol foam.

18. Composition according to claim 1, wherein the composition additionally contains additives which are foam reinforcers, thickeners, sequestering agents, electrolytes, fragrances, preservatives, fatty alcohols, mineral oils or waxes, vegetable oils or waxes, animal oils or waxes, synthetic oils or waxes, ceramides, UV screening agents, agents for combating free radicals, pearlescence agents, biocides, antibacterials, antidandruff agents, antiseborrheic agents, antiparasitic agents, repellents, dyes, pigments, oxidizing agents, reducing agents, moisturizers, anionic, nonionic or cationic polymers, vitamins or α-hydroxy acids.

19. Process for cosmetic washing and/or conditioning of the hair or of the skin, comprising applying an effective amount of a composition according to claim 1 to the skin or the hair and then optionally rinsing the hair or skin with water.

* * * * *